United States Patent

Reuven

Patent Number: 5,850,636
Date of Patent: Dec. 22, 1998

[54] HEATABLE HAIR CAP

[76] Inventor: Michelle G. Reuven, 4219 E. 4th St. #5, Long Beach, Calif. 90814

[21] Appl. No.: 1,441

[22] Filed: Dec. 31, 1997

[51] Int. Cl.$^6$ ........................................................ A42B 1/04
[52] U.S. Cl. ................................. 2/174; 2/171.2; 2/200.1; 2/200.2; 607/109; 607/110
[58] Field of Search .............................. 2/7, 171.2, 174, 2/200.1, 200.2; 607/109, 110

[56] References Cited

U.S. PATENT DOCUMENTS

| | | | |
|---|---|---|---|
| 3,070,803 | 1/1963 | Slepicka | 2/7 |
| 4,552,149 | 11/1985 | Tatsuki | 607/110 |
| 4,854,319 | 8/1989 | Tobin | 2/171.2 |
| 5,605,144 | 2/1997 | Simmons et al. | 607/109 |

Primary Examiner—Diana L. Biefeld

[57] ABSTRACT

A new heatable hair cap for providing heat to a wearer's head to aid in the styling of the wearer's hair. The inventive device includes a cap member having an interior layer and an exterior layer defining a cap member interior space between them. Provided within the cap member interior space is a heatable gel solution for providing heat to the head cavity.

16 Claims, 3 Drawing Sheets

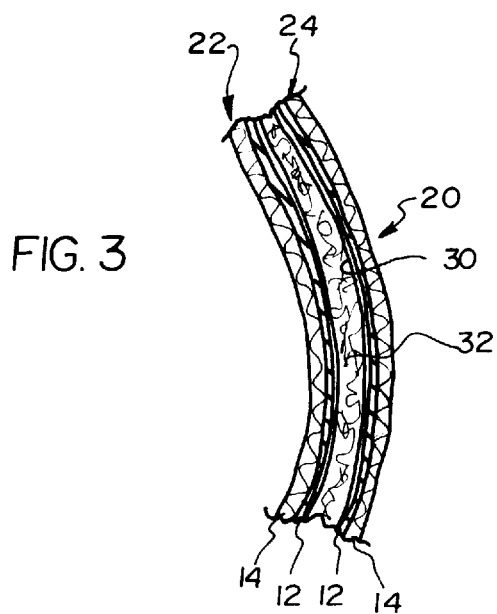
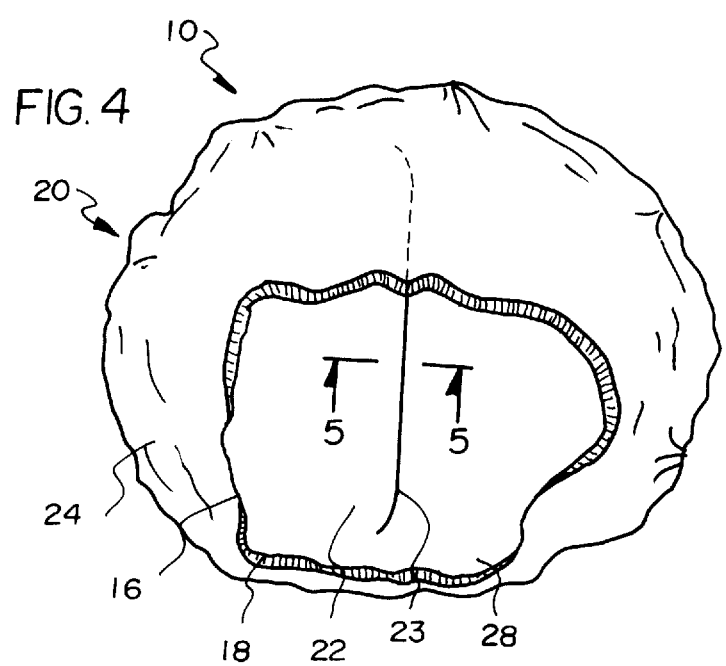

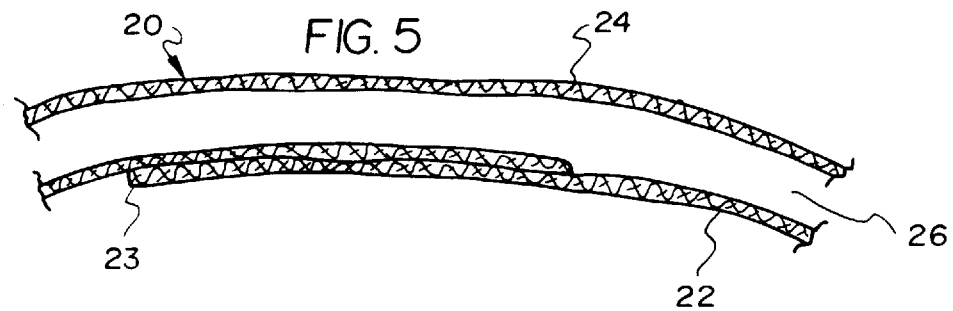
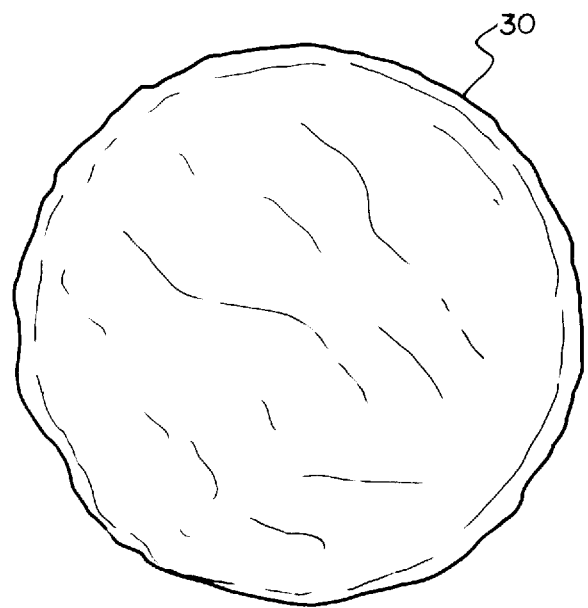

HEATABLE HAIR CAP

BACKGROUND OF THE INVENTION

1. Field of the Invention

The present invention relates to heatable hair caps and more particularly pertains to a new heatable hair cap for providing heat to a wearer's head to aid in the styling of the wearer's hair.

2. Description of the Prior Art

The use of heatable hair caps is known in the prior art. More specifically, heatable hair caps heretofore devised and utilized are known to consist basically of familiar, expected and obvious structural configurations, notwithstanding the myriad of designs encompassed by the crowded prior art which have been developed for the fulfillment of countless objectives and requirements.

Known prior art heatable hair caps include U.S. Pat. No. 4,061,898; U.S. Pat. No. 4,783,866; U.S. Pat. No. Des. 243,800; U.S. Pat. No. 5,265,278; U.S. Pat. No. 4,756,311; and U.S. Pat. No. 4,459,471.

While these devices fulfill their respective, particular objectives and requirements, the aforementioned patents do not disclose a new heatable hair cap. The inventive device includes a cap member having an interior layer and an exterior layer defining a cap member interior space between them. Provided within the cap member interior space is a heatable gel solution for providing heat to the head cavity.

In these respects, the heatable hair cap according to the present invention substantially departs from the conventional concepts and designs of the prior art, and in so doing provides an apparatus primarily developed for the purpose of providing heat to a wearer's head to aid in the styling of the wearer's hair.

SUMMARY OF THE INVENTION

In view of the foregoing disadvantages inherent in the known types of heatable hair caps now present in the prior art, the present invention provides a new heatable hair cap construction wherein the same can be utilized for providing heat to a wearer's head to aid in the styling of the wearer's hair.

The general purpose of the present invention, which will be described subsequently in greater detail, is to provide a new heatable hair cap apparatus and method which has many of the advantages of the heatable hair caps mentioned heretofore and many novel features that result in a new heatable hair cap which is not anticipated, rendered obvious, suggested, or even implied by any of the prior art heatable hair caps, either alone or in any combination thereof.

To attain this, the present invention generally comprises a cap member having an interior layer and an exterior layer defining a cap member interior space between them. Provided within the cap member interior space is a heatable gel solution for providing heat to the head cavity.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new heatable hair cap apparatus and method which has many of the advantages of the heatable hair caps mentioned heretofore and many novel features that result in a new heatable hair cap which is not anticipated, rendered obvious, suggested, or even implied by any of the prior art heatable hair caps, either alone or in any combination thereof.

It is another object of the present invention to provide a new heatable hair cap which may be easily and efficiently manufactured and marketed.

It is a further object of the present invention to provide a new heatable hair cap which is of a durable and reliable construction.

An even further object of the present invention is to provide a new heatable hair cap which is susceptible of a low cost of manufacture with regard to both materials and labor, and which accordingly is then susceptible of low prices of sale to the consuming public, thereby making such heatable hair cap economically available to the buying public.

Still yet another object of the present invention is to provide a new heatable hair cap which provides in the apparatuses and methods of the prior art some of the advantages thereof, while simultaneously overcoming some of the disadvantages normally associated therewith.

Still another object of the present invention is to provide a new heatable hair cap for providing heat to a wearer's head to aid in the styling of the wearer's hair.

Yet another object of the present invention is to provide a new heatable hair cap which includes a cap member having an interior layer and an exterior layer defining a cap member interior space between them. Provided within the cap member interior space is a heatable gel solution for providing heat to the head cavity.

Still yet another object of the present invention is to provide a new heatable hair cap that provides heats for hair oil treatments to aid deep penetration of the oil into the hair.

Even still another object of the present invention is to provide a new heatable hair cap that may be used instead of a hood-type hair dryer while conditioning or coloring hair.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of the cap member of the present invention as seen from line 3—3 on FIG. 2.

FIG. 4 is a schematic side view of an embodiment of the present invention with a flapped opening into the cap member interior space.

FIG. 5 is a schematic cross-sectional view of the flapped opening of the present invention taken from line 5—5 of FIG. 4.

FIG. 6 is a schematic top side view of a circular flexible container of the present invention.

DESCRIPTION OF THE PREFERRED EMBODIMENT

Figure 1:
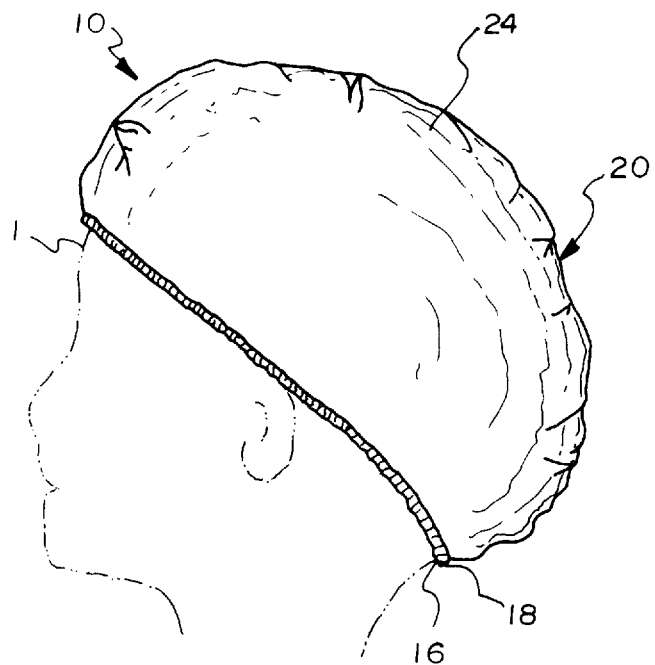
FIG. 1 is a schematic side view of a new heatable hair cap being worn on a head according to the present invention.

With reference now to the drawings, and in particular to FIGS. 1 through 6 thereof, a new heatable hair cap embodying the principles and concepts of the present invention and generally designated by the reference numeral 10 will be described.

As best illustrated in FIGS. 1 through 6, the heatable hair cap 10 generally comprises a cap member 20 having an interior layer 22 and an exterior layer 24 defining a cap member interior space 26 between them. Provided within the cap member interior space is a heatable gel solution 32 for providing heat to the head cavity 28.

The cap member 20 has interior and exterior layers 22,24 that define a cap member interior space 26 between them. As shown in FIG. 3, the interior and exterior layers 22,24 preferably each include inner and outer sublayers 12,14 with the inner sublayers 12 of the interior and exterior layers 22,24 positioned adjacent the cap member interior space 26. Ideally, the inner sublayers 12 are made of a rubber while the outer sublayers 14 are made a cloth material, of either a natural or synthetic fabric. In this ideal embodiment, it is important that the inner and outer sublayers 12,14 are made of materials that are microwavable.

Figure 2:
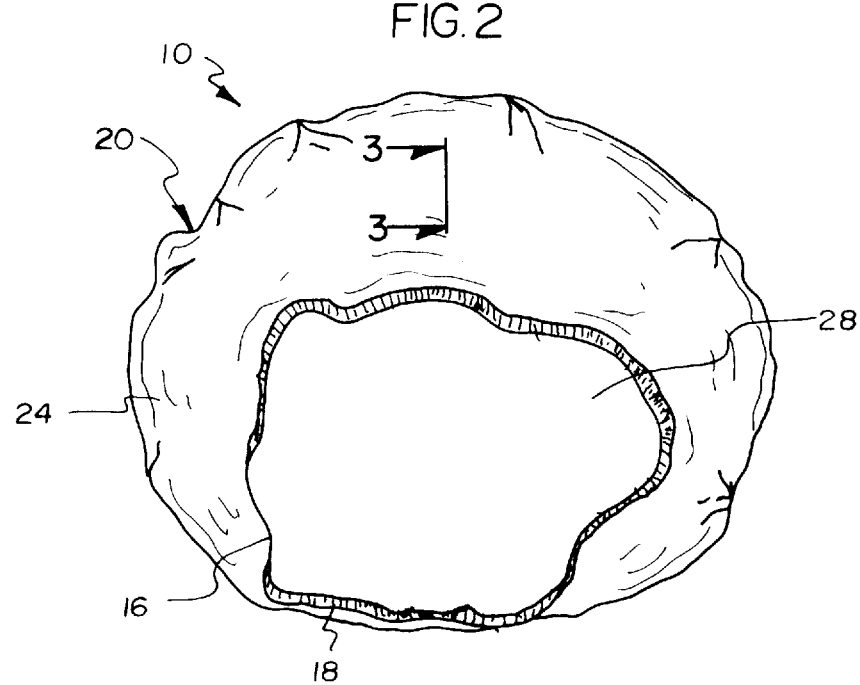
FIG. 2 is a schematic front side view of the present invention.

As shown in FIG. 2, the interior layer 22 of the cap member 20 forms a head cavity 28 for receiving the scalp portion of a head 1 therein with the lower periphery 16 of the cap member 20 defining an opening into the head cavity 28. Preferably, the lower periphery 16 of the cap member 20 includes an elongate flexible member 18 that is formed into an annular ring around the lower periphery 16. The flexible member 18 is stretchable along its length to help hold the cap member 20 to a head 1 inserted into the head cavity 28.

Within the cap member interior space 26 is a heatable gel solution 32 for providing heat to the head cavity 28. Preferably, the heatable gel solution 32 is a solution formulated to retain hot or cold temperatures for a substantial period of time. An illustrative gel solution 32 is the solution commonly know as "Blue Ice". Preferably, the gel solution 32 is heatable by either microwaving the gel for a period of time or boiling the gel in water for a period of time. In a preferred embodiment of the invention, the gel solution 32 is contained within a flexible container 30 provided within the cap member interior space 26. The flexible container 30 is preferably shaped to fit the cap member interior space 26 and, ideally, may be circular in shape, as shown in FIG. 6.

As shown in FIGS. 4 and 5 in an ideal embodiment of the invention, the interior layer 22 of the cap member 20 has an opening into the cap member interior space 26 and a flap 23 covering the opening of the interior layer 22 into the cap member interior space 26. This flapped opening 23 permits removable insertion of the flexible container 30 into cap member interior space 26 through the opening of the interior layer 22.

In use, the gel solution 32 is heated either by microwaving the entire cap 10 or just the flexible container 30. Optionally, the flexible container 30 may be boiled in water to heat the gel solution 32. The flexible container 30 is inserted into the cap member interior space 26 and the cap 10 is then worn on the head of a person to provide heat to the person's hair and scalp.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heatable hair cap, comprising:

a cap member having an interior layer and an exterior layer, said interior and exterior layers of said cap member defining a cap member interior space therebetween;

said interior layer of said cap member forming a head cavity for receiving a portion of a head therein, said cap member having a lower periphery defining an opening into said head cavity;

a heatable gel solution being provided in said cap member interior space for providing heat; and a flexible container being provided in said cap member interior space said heatable gel solution being contained in said flexible container.

2. The heatable hair cap of claim 1, wherein said interior and exterior layers each include inner and outer sublayers, said inner sublayers of said interior and exterior layers being positioned adjacent said cap member interior space.

3. The heatable hair cap of claim 2, wherein said inner sublayers comprise rubber.

4. The heatable hair cap of claim 3, wherein said outer sublayers comprise a cloth material.

5. The heatable hair cap of claim 1, wherein said lower periphery of said cap member has an elongate flexible member being formed into an annular ring therearound, said flexible member being stretchable along its length to help hold said cap member to a head inserted into said head cavity of said cap member.

6. The heatable hair cap of claim 1, wherein said flexible cap is circular.

7. The heatable hair cap of claim 1, wherein said flexible container is shaped to fit said cap member interior space.

8. The heatable hair cap of claim 1, wherein said interior layer of said cap member has an opening into said cap member interior space, wherein said flexible container is removably insertable into cap member interior space through said opening of said interior layer.

9. The heatable hair cap of claim 8, wherein said interior layer of said cap member has a flap covering said opening of said interior layer into said cap member interior space.

10. A heatable hair cap, comprising:
- a cap member having an interior layer and an exterior layer, said interior and exterior layers of said cap member defining a cap member interior space therebetween;
- said interior layer of said cap member forming a head cavity for receiving a portion of a head therein, said cap member having a lower periphery defining an opening into said head cavity;
- wherein said interior and exterior layers each include inner and outer sublayers, said inner sublayers of said interior and exterior layers being positioned adjacent said cap member interior space;
- wherein said inner sublayers comprise rubber;
- wherein said outer sublayers comprise a cloth material;
- said lower periphery of said cap member having an elongate flexible member being formed into an annular ring therearound, said flexible member being stretchable along its length to help hold said cap member to a head inserted into said head cavity of said cap member; and
- a flexible container being provided in said cap member interior space, said flexible container being shaped to fit said cap member interior space, said flexible container including a heatable gel solution therein for providing heat;
- said interior layer of said cap member having an opening into said cap member interior space, wherein said flexible container is removably insertable into cap member interior space through said opening of said interior layer; and
- said interior layer of said cap member having a flap covering said opening of said interior layer into said cap member interior space.

11. A heatable hair cap, comprising:
- a cap member having an interior layer and an exterior layer, said interior and exterior layers of said cap member defining a cap member interior space therebetween;
- said interior layer of said cap member forming a head cavity for receiving a portion of a head therein, said cap member having a lower periphery defining an opening into said head cavity;
- a heatable gel solution being provided in said cap member interior space for providing heat;
- wherein said interior and exterior layers each include inner and outer sublayers, said inner sublayers of said interior and exterior layers being positioned adjacent said cap member interior space;
- wherein said inner sublayers comprise rubber; and
- wherein said outer sublayers comprise a cloth material.

12. The heatable hair cap of claim 11, further comprising a flexible container being provided within said cap member interior space, said heatable gel solution being contained within said flexible container.

13. The heatable hair cap of claim 12, wherein said flexible cap is circular.

14. The heatable hair cap of claim 12, wherein said flexible container is shaped to fit said cap member interior space.

15. The heatable hair cap of claim 12, wherein said interior layer of said cap member has an opening into said cap member interior space, wherein said flexible container is removably insertable into cap member interior space through said opening of said interior layer.

16. The heatable hair cap of claim 15, wherein said interior layer of said cap member has a flap covering said opening of said interior layer into said cap member interior space.

* * * * *